United States Patent
Mackie et al.

(10) Patent No.: US 7,519,149 B2
(45) Date of Patent: Apr. 14, 2009

(54) SMALL FIELD INTENSITY MODULATED RADIATION THERAPY MACHINE

(75) Inventors: Thomas R. Mackie, Verona, WI (US); Stewart J. Becker, New York, NY (US); Robert Jeraj, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/576,358

(22) PCT Filed: Mar. 27, 2006

(86) PCT No.: PCT/US2006/011110

§ 371 (c)(1),
(2), (4) Date: Mar. 30, 2007

(87) PCT Pub. No.: WO2006/107637

PCT Pub. Date: Oct. 12, 2006

(65) Prior Publication Data

US 2007/0242801 A1    Oct. 18, 2007

Related U.S. Application Data

(60) Provisional application No. 60/667,480, filed on Apr. 1, 2005.

(51) Int. Cl.
*A61N 5/10* (2006.01)

(52) U.S. Cl. .......................................... 378/65; 378/37

(58) Field of Classification Search ............... 378/4–20, 378/37, 65
See application file for complete search history.

(56) References Cited

U.S. PATENT DOCUMENTS

| | | | |
|---|---|---|---|
| 4,726,046 A | 2/1988 | Nunan et al. | |
| 5,267,294 A | 11/1993 | Kuroda et al. | |
| 6,463,122 B1 | 10/2002 | Moore | |
| 2008/0187095 A1* | 8/2008 | Boone et al. | 378/37 |

FOREIGN PATENT DOCUMENTS

| | | |
|---|---|---|
| EP | 1 057 499 | 12/2000 |
| GB | 2 068 700 | 8/1981 |
| WO | WO 97/13552 | 4/1997 |

OTHER PUBLICATIONS

PCT Search Report for PCT/US2006/011110.

* cited by examiner

*Primary Examiner*—Courtney Thomas
(74) *Attorney, Agent, or Firm*—Quarles & Brady LLP; Benjamin J. Peirce

(57) ABSTRACT

A small field radiation therapy machine having an aperture diameter of 30 cm or less provides improved ray definition for specialized treatment of portions of the human body such as head a breast.

18 Claims, 2 Drawing Sheets

SMALL FIELD INTENSITY MODULATED RADIATION THERAPY MACHINE

CROSS-REFERENCE TO RELATED APPLICATIONS

This application is based on provisional application 60/667,480 filed Apr. 1, 2005 and entitled "Limited Field Tomotherapy Machine" and claims the benefit thereof.

STATEMENT REGARDING FEDERALLY SPONSORED RESEARCH OR DEVELOPMENT

This invention was made with United States government support awarded by the following agency: NIH CA 088960. The United States has certain rights in this invention.

BACKGROUND OF THE INVENTION

The present invention relates to radiation therapy machines for treatment of tumors and the like and in particular to an intensity modulated radiation (IMRT) therapy machine for specialized treatment of portions of the body.

In external beam radiation therapy, high-energy radiation is directed through a patient to the site of a tumor. Multiple beams intersecting at site of a tumor may be used to reduce the dose to the skin and other intervening tissue. The individual beams may be collimated to the outline of the tumor to further reduce exposure of healthy tissue surrounding the tumor.

In intensity modulated radiation therapy (IMRT) the intensity of individual rays within the beams is adjusted to produce more complex dose patterns resulting not simply from the juxtaposed outlines of the beams but from the additive overlay of the rays of different intensities within the beams.

In Tomotherapy, an extremely large number of beams are directed through 360 degrees toward the patient from the rotation plane and the patient is treated in a series of slices. Individually modulated rays within each beam provide precise irradiation of irregular tumor shapes at greater speed and accuracy than conventional IMRT designs.

Tomotherapy machines and techniques are described in U.S. patents: U.S. Pat. No. 6,636,622 "Method and apparatus for calibration of radiation therapy equipment and verification of radiation treatment; U.S. Pat. No. 6,618,467 "Megavoltage computed tomography during radiotherapy"; U.S. Pat. No. 6,560,311 "Method for preparing a radiation therapy plan"; U.S. Pat. No. 6,438,202 "Method using post-patient radiation monitor to verify entrance radiation and dose in a radiation therapy machine"; U.S. Pat. No. 6,385,286 "Delivery modification system for radiation therapy"; U.S. Pat. No. 6,345,114 "Method and apparatus for calibration of radiation therapy equipment and verification of radiation treatment"; U.S. Pat. No. 5,724,400 Radiation therapy system with constrained rotational freedom"; U.S. Pat. No. 5,673,300 "Method of registering a radiation treatment plan to a patient"; U.S. Pat. No. 5,661,773 "Interface for radiation therapy machine"; U.S. Pat. No. 5,625,663 "Dynamic beam flattening apparatus for radiation therapy"; U.S. Pat. No. 5,548,627 "Radiation therapy system with constrained rotational freedom"; U.S. Pat. No. 5,442,675 "Dynamic collimator for radiation therapy"; U.S. Pat. No. 5,394,452 Verification system for radiation therapy"; and U.S. Pat. No. 5,317,616 "Method and apparatus for radiation therapy"; all assigned to the assignee of the present invention and hereby incorporated by reference.

While Tomotherapy provides for a high degree of accuracy and precision in the placement of dose, standard radiation therapy gantries, moveable in multiple dimensions, may be preferred for certain treatments, for example, treatments of breast tumors, where out-of-plane gantry locations may limit exposure of the patient's chest cavity. In this case, precision of dose placement is traded off against the ability to limit dose to other body structures.

The increased accuracy of current Tomotherapy systems is limited by physical constraints related to creating narrower occluding leaves, such as define the width of the modulated rays within each radiation beam, accurately locating the tumor, accommodating a range of patient body sizes, and controlling for patient motion.

BRIEF SUMMARY OF THE INVENTION

The present inventors have recognized that the benefits of Tomotherapy can be expanded through the use of a Tomotherapy machine having a shortened source to rotation axis distance. First, by shortening this distance, the gantry may be made sufficiently compact to be maneuvered to be positioned around the particular body part, for example, the breast requiring treatment, thus eliminating the need for generalized exposure to the patient's torso. Second, by reducing this distance, narrower rays are naturally created without changing the shutter structure. The improved resolution made possible, is particularly well-suited for treatment of tumors in the head or the breast, where more precise control of dose patterns can be beneficial and meaningful because patient motion may be more readily controlled in these parts of the body.

Specifically then, the present invention provides a small field radiation therapy machine having a radiation source producing a radiation beam directed along a beam axis from a radiation origin. A support rotatably guides the radiation origin to be constrained within a rotation plane about a rotation axis so that the beam axis is directed across the rotation axis and the radiation origin is separated from the rotation axis by no more than 60 centimeters, substantially less than the 85 centimeters required for full-body Tomotherapy machines. A beam modulator independently controls radiation fluence of multiple rays within the radiation beam.

Thus it is one object of at least one embodiment of the invention to provide a system particularly suited for radiation therapy of the head or breast.

The radiation therapy machine may include a patient support providing an opening extending into the rotation plane and sized for the admission and stabilization of a body member of a patient.

It is thus an object of at least one embodiment of the invention to provide a system that may provide support that is well adapted to treatment of particular portions of the anatomy.

The body member may be a human head.

Thus it is an object of at least one embodiment of the invention to provide a system well suited for high-resolution radiation therapy of the human head.

The rotation plane may be substantially vertical and the radiation therapy machine may include a table for supporting the patient in a supine position with an opening of the patient support attached at one end of the table.

It is thus another object of at least one embodiment of the invention to provide a simple, self-contained system for treating brain tumors that allows the patient to rest in a comfortable supine position.

The body member may be a human breast.

Thus it is an object of at least one embodiment of the invention to allow Tomotherapy as a treatment option for breast tumors.

The rotation plane may be substantially horizontal and the system may include a table for supporting the patient in a horizontal position with one breast passing downward through an opening in the table providing the patient support.

Thus it is an object of at least one embodiment of the invention to provide an integrated device for treatment of breast tumors to allow a comfortable attitude of the patient that promotes extension of the breast from the chest wall, for example by having a bowl-shaped table The beam modulator may be a series of bi-stable shutters blocking or passing rays of the beam to control an average fluence for the rays. The shutters may be built into the jaws defining the field width and providing primary collimation for the beam.

It is thus another object of at least one embodiment of the invention to provide a simple modulator mechanism that may work within the compact space of the present invention. It is a further object of the invention to allow precise radiation treatment, for example near the chest wall for one breast, where conformal treatment, using multileaf collimators to outline a tumor shape, is not practical because of the inability to move shutters into the space occupied by the patient's chest wall.

The support may include a bearing providing a race having a diameter greater than 60 cm.

It is another object of at least one embodiment of the invention to provide an extremely stable rotating platform suitable for high-resolution dose placement.

The beam modulator may provide for at least 16 independently modulated rays and/or the modulated rays may have a width at the rotation axis measured along the rotation plane of no more than 0.6 cm.

It is thus another object of at least one embodiment of the invention to provide an extremely high-resolution radiation therapy system with commercially practical modulator mechanisms.

The beam axis may be a centerline of the beam and tipped with respect to the rotation plan.

Thus it is an object of at least one embodiment of the invention to provide as close to full coverage as possible of breast tissue up to the chest wall when the device is used in breast imaging.

The radiation source may be a linear accelerator providing a static portion arranged to accelerate electrons along the rotation axis and the rotating coupling to a wave-guide rotating with the support.

It is another object of at least one embodiment of the invention to provide a low inertia, simplified radiation source for a small field radiation therapy machine that may thus work in confined spaces.

The support may provide the radiation shield extending along the radiation beam to one side of the radiation beam adjacent to the patient.

It is thus another object of at least one embodiment of the invention to allow the patient to be placed close to the radiation source for example for treatment of breast tumors and the like while moderating unintentional radiation exposure to the patient.

The radiation source may provide an energy of less than 5 MV. Thus it is another object of at least one embodiment of the invention to reduce the expense of the Tomotherapy system by allowing a lower energy linear accelerator or an isotope source such as Co-60.

The linear accelerator may be in-line with the axis or displaced and oriented in a different location, with magnetic beam handling to bring the beam to be directed to the target and pointing toward the axis of rotation.

Thus it is another object of the invention to provide increased flexibility in orienting the radiotherapy equipment with respect to the patient.

These particular objects and advantages may apply to only some embodiments falling within the claims and thus do not define the scope of the invention.

DETAILED DESCRIPTION OF THE PREFERRED EMBODIMENT

Figure 1:
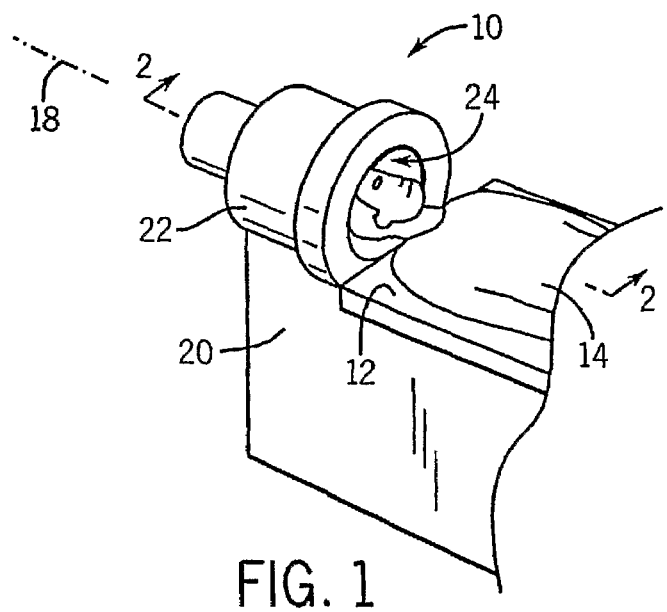
FIG. 1 is a fragmentary perspective view of a first embodiment of the invention adapted to treatment of a patient's head.

Referring now to FIG. 1, a first embodiment of the small field radiation therapy device 10 provides a patient table 12 for supporting a patient 14 along a longitudinal rotation axis 18.

Figure 2:
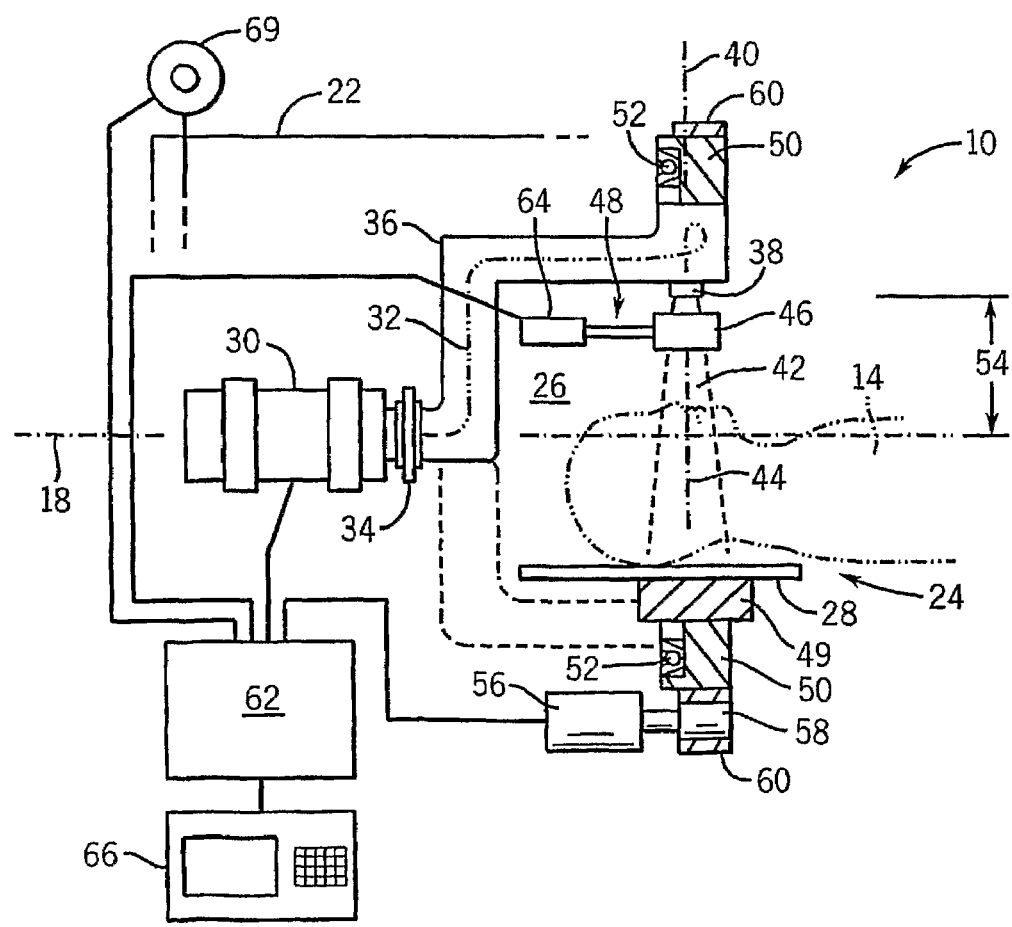
FIG. 2 is a cross-sectional view along line 2-2 of FIG. 1 showing configuration of a rotating wave-guide allowing a stationary linear accelerator to drive a radiation source that orbits about the patient's head on a gantry that is supported by an outboard bearing.

Referring also to FIG. 2, the table 12 is supported on a base 20 that also holds a gantry housing 22 at one end of the table 12. The gantry housing 22 provides an opening 24 sized to receive the patient's head into a cavity 26 along the longitudinal axis. The cavity 26 provides a head support 28 employing radiolucent restraining cushions immobilizing the patient's head against rotation and unwanted movement during treatment.

A stationary linear accelerator 30 is positioned at a superior end of the gantry housing 22 to direct the stream of electrons 32 along the rotation axis 18 toward the patient 14. The electrons 32 are received by a rotating coupling 34 which connects the stationary linear accelerator 30 to a wave-guide 36. The wave-guide 36 extends initially along the rotation axis 18 from the linear accelerator 30, then in a dog-legged fashion perpendicularly to the rotation axis 18 and then again parallel to the rotation axis 18. The wave-guide 36 ends at a target 38 with the electrons striking the target 38 create a beam 42 of radiation extending from a radiation source point of the target 38 along a beam axis 44. The beam axis 44 is perpendicular to the rotation axis 18 and parallel to a rotation plane 40 passing through a portion of the patient's head when the patient is positioned within the cavity 26. A separation distance 54 between the target 38 and the rotation axis 18 is constrained to less than 60 cm and may be as little as 30 cm. This is in contrast to a more typical separation distance of 85 cm necessary to accommodate a patient's entire torso.

The target 38 may be tungsten, however preferably beryllium is used. Although beryllium has a much lower density than tungsten and a substantially lower radiation yield, for this machine, the proportion of radiation directed in forward direction versus a lateral direction is important because, in one embodiment, the patient's untreated chest wall is located close to the beam. Beryllium has a forward fluence rate 60% of that of tungsten but a substantially lower lateral fluence making it ideal for this machine.

Upon leaving the target 38, the beam 42 passes through shutters 46 of a shutter assembly 48, to be described, and then through the patient's head held in the head support 28. The beam 42 passes through the patient's head to be stopped by a shield 49 positioned on the opposite side of the patient's head.

The portion of the wave-guide 36 containing the target 38, the shutter assembly 48, and shield 49 are all supported on a gantry ring 50 lying within the rotation plane 40 and supported at its outer periphery by support bearings 52. In the preferred embodiment, the interface between the sliding surfaces of the bearings 52 such as may introduce some mechanical play in the rotation of the gantry ring 50, and which provide the effective "race" of the bearing system, is of greater radius than the opening 24 so as to minimize bearing induced out-of-plane movement of the target 38. Positioning the bearings 52 at the outer periphery of the gantry ring 50 allows extremely stable and simple rotation of the gantry ring 50 with play in the bearings minimized by their location at the outer end of an effective lever arm.

The bearings 52 allow rotation of the gantry ring 50 in the rotation plane 40 so that the beam axis 44 can be swept through a range of angles of 360° about the rotation axis 18 with the target 38 opposed to the shield 49 at all rotational positions. The rotating coupling 34 allows the wave-guide 36 to move with the gantry ring 50 to provide electrons to the target 38 without movement of the linear accelerator 30 or its associated power supply or control electronics.

A motor 56 drives a sprocket 58 communicating with a timing belt 60 or the like engaging teeth on the outer periphery of the gantry ring 50 allowing the gantry to be controllably rotated for example by a stepper or servo motor under the control of a central controller 62.

Central controller 62 also controls application of radiation to the patient 14 by control lines to the linear accelerator 30 and control lines to actuators 64 that may move the individual shutters 46 into and out of the radiation beam 42.

The shutters 46 provide for a division of the beam 42 into a plurality of individually controllable rays arranged in fan like manner along the rotation plane 40 so as to allow for high-speed intensity modulated radiation therapy. Shutters of this type are described in the U.S. patents cited in the Background of the Invention, above, all assigned to the assignee of the present invention and hereby incorporated by reference. Generally controlling the relative proportion of time that the shutters 46 block and unblock the various rays of the beam 42, the effective irradiation of the patient 14 by each ray may be controlled allowing sophisticated dose placement.

Ideally, the shutters 46 have a thickness that will produce standard beam widths of about 0.61 cm at the isocenter of the device 10 (or more generally a beam width within a standard range of 0.5 cm to 2.0 cm). In this case, the reduced bore size and field of the device 10 allows for a significant reduction in the required number of shutters 46 from a standard number of shutters of about 64 to a reduced number of shutters of 32 or 18 or less, although typically there will be 16 or more shutters 46. Alternatively, the number of shutters 46 may be increased over this reduced number, for example, remaining at 64 shutters, to permit narrower beam widths of less than 0.61 cm or 0.5 cm at the isocenter of the device 10 (or more generally within a range of 0.25 to 1 cm) allowing for higher resolution dose placement.

An operator console 66 may provide for manual control of the small field radiation therapy device 10 as well as the loading of data (sinograms) for the control of the shutter assembly 48 according to methods known in the art.

The ability to effectively immobilize the patient's head with respect to patient movement and physiological motion caused by movement of the lungs and heart, allows the narrow ray size obtained by the shortening of the separation distance 54 to be used effectively.

A second motor 69 may be attached to the housing 22 to allow the housing 22 and gantry ring 50 to move with respect to the base 20 and patient head support 28 thereby allowing different slices of the patient's head to be sequentially or helically treated. By moving the housing 22 and not the patient 14, patient comfort may be increased, and unintended shifting of the patient decreased during the treatment operation.

In an alternative embodiment, not shown, the shield 49 may be augmented with a portal imaging device for the collection of megavoltage CT-type images also processed by controller 62 or a separate computer tomography system including an x-ray tube and opposed kilovoltage detector may be placed, for example perpendicularly to the placement of the target 38 and shield 49 on the gantry ring 50.

Figure 3:
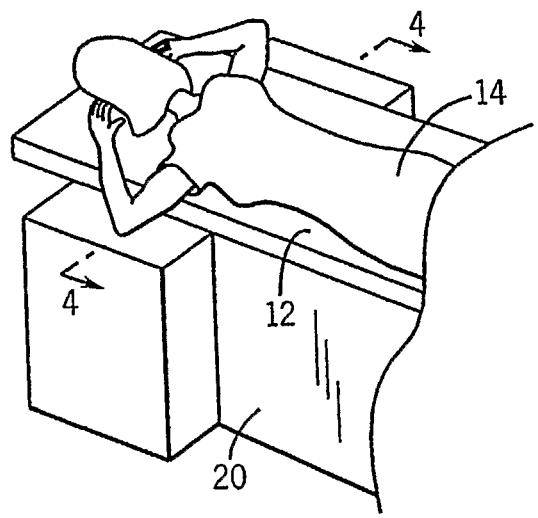
FIG. 3 is a figure similar to that of FIG. 1 showing an alternative embodiment of the invention adapted to treatment of the breast.
Figure 4:
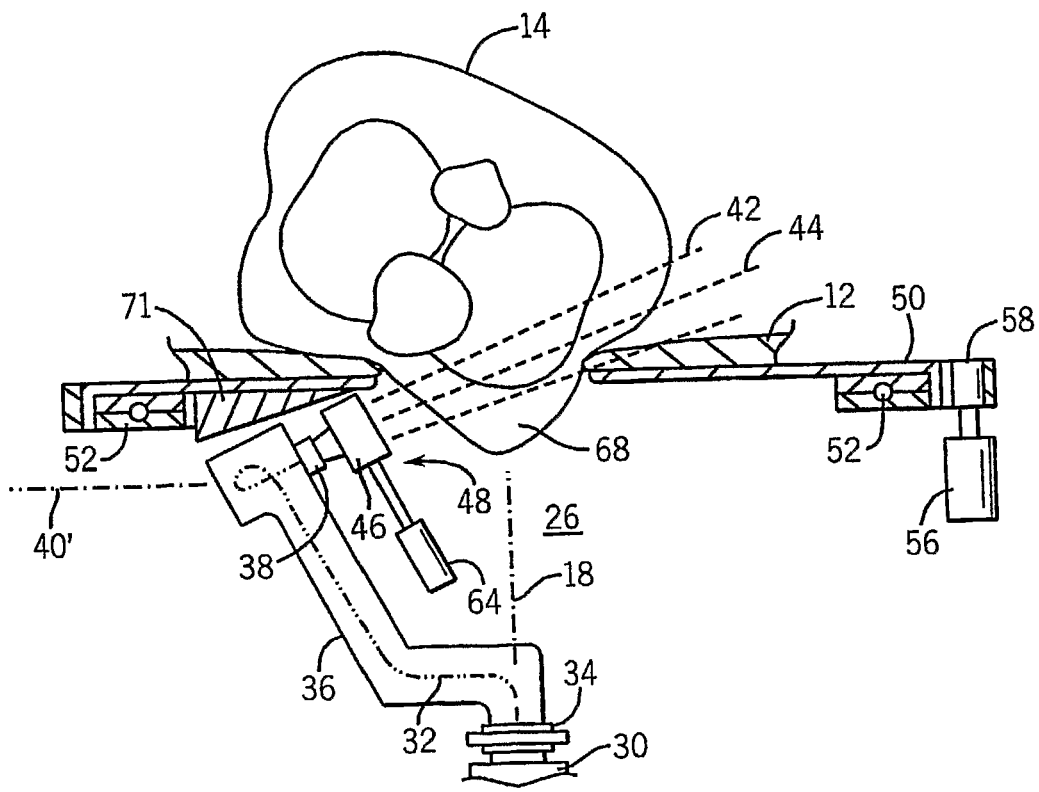
FIG. 4 is a cross-sectional view along line 4-4 of FIG. 3 showing support of the breast and angulation of the beam from the rotation plane.

Referring now to FIG. 3, the small opening size of the radiation therapy device 10 described above allows the rotation plane 40' to be shifted to a near horizontal position as shown in FIG. 4, for example, beneath the patient table 12 for radiation therapy of the breast 68. In this embodiment, the patient table 12 may provide a support for the breast 68 that allows the breast 68 to descend through the table 12 when the patient is supine on the table in a face down position. The table may have a bowl shape (not shown) around a hole through which the breast 68 descends to improve the separation of the torso of the patient from the beam.

For treatment of the breast 68, the wave-guide 36 is tipped outward or the target 38 angled so as to direct the beam axis 44 at an angle with respect to the rotation plane 40' upwards slightly towards the patient. In this way exposure of the breast tissue near the chest wall may be ensured without obstruction from the table 12 or gantry ring 50. A patient shield 71 may be positioned above the target 38 and the shutters 46 along the side of the radiation beam 42 to prevent scatter radiation from passing into the patient 14 who lies closely adjacent to the rotation plane 40'. The table 12 may also provide shielding.

Again motion of the gantry ring 50 with respect to the table 12 may be provided by a motor (not shown) to allow for treatment of the breast 68 in a series of vertically displaced slices.

It will be understood from this description, that the geometry that allows greater ray resolution as the separation distance 54 is reduced, also makes it possible to provide a reduced cost Tomotherapy machine reducing the number of shutters to provide comparable resolution to that of a whole body system.

It is specifically intended that the present invention not be limited to the embodiments and illustrations contained herein, but include modified forms of those embodiments including portions of the embodiments and combinations of elements of different embodiments as come within the scope of the following claims.

We claim:

1. A small field radiation therapy machine comprising:
   a radiation source providing a radiation beam directed along a beam axis from a radiation origin;
   a support rotatably guiding the radiation origin to be constrained within a rotation plane about a rotation axis, so that the beam axis is directed across a rotation axis and the radiation origin is separated from the rotation axis by no more than 60 cm; and a beam modulator independently controlling the radiation fluence of multiple rays within the radiation beam.

2. The small field radiation therapy machine of claim 1 further including a patient support providing an opening extending into the rotation plane and sized for admission of a body member of a patient.

3. The small field radiation therapy machine of claim 2 wherein the body member is a human head.

4. The small field radiation therapy machine of claim 3 wherein the rotation plane is substantially vertical.

5. The small field radiation therapy machine of claim 3 further including a table for supporting the patient in a horizontal position with the opening of the patient support attached at one end of the table.

6. The small field radiation therapy machine of claim 2 wherein the body member is a human breast.

7. The small field radiation therapy machine of claim 6 wherein the rotation plane is substantially horizontal.

8. The small field radiation therapy machine of claim 6 further including a table for supporting a patient in a horizontal position with one breast passing downward through an opening in the table providing the patient support.

9. The small field radiation therapy machine of claim 1 wherein the beam modulator is a series of bi-stable shutters blocking or passing rays of the beam to control the fluence for the rays.

10. The small field radiation therapy machine of claim 1 wherein the support includes a bearing providing a race having a diameter greater than 60 cm.

11. The small field radiation therapy machine of claim 1 wherein the beam modulator provides for at least 16 independently modulated rays.

12. The small field radiation therapy machine of claim 1 wherein the beam modulator provides or independently modulated rays having a width at the rotation axis measured along the rotation plane of no more than 0.6 cm.

13. The small field radiation therapy machine of claim 1 wherein the beam axis is a centerline of the beam and is tipped with respect to the rotation plane.

14. The small field radiation therapy machine of claim 1 wherein the radiation source is a linear accelerator providing static portion arranged to accelerate electrons along the rotation axis and a rotating coupling to a wave guide rotating with the support.

15. The small field radiation therapy machine of claim 1 wherein the support provides a radiation shield extending along the radiation beam to one side of the radiation beam adjacent to a patient.

16. The small field radiation therapy machine of claim 1 including a radiation shield blocking radiation from the radiation source to a chest wall of a patient.

17. The small field radiation therapy machine of claim 1 wherein the radiation source provides a beam energy of not more than 5 MV.

18. The small field radiation therapy machine of claim 1 wherein the radiation source is a radioactive isotope.

* * * * *